United States Patent [19]
Kraus

[11] Patent Number: 5,586,884
[45] Date of Patent: Dec. 24, 1996

[54] DENTAL ARTICULATOR

[76] Inventor: Richard F. Kraus, 3 Oakbrook Club Dr., #D 106, Oakbrook, Ill. 60521

[21] Appl. No.: 296,736

[22] Filed: Aug. 26, 1994

[51] Int. Cl.$^6$ .................................................. A61C 11/00
[52] U.S. Cl. .................. 433/60; 433/57; 433/63
[58] Field of Search ................................ 433/54, 57, 60, 433/61, 62, 63, 65, 66, 67, 58, 64

[56] References Cited

U.S. PATENT DOCUMENTS

| | | |
|---|---|---|
| 1,574 | 4/1840 | Cameron .................................... 433/63 |
| 175,046 | 3/1876 | Davidson . |
| D. 204,381 | 4/1966 | Orofino .................................... D24/1 |
| 772,304 | 10/1904 | Williams . |
| 1,022,055 | 4/1912 | Weiss ........................................ 433/65 |
| 1,553,492 | 9/1925 | Williams . |
| 2,180,673 | 11/1939 | Galetti . |
| 2,423,522 | 7/1948 | Shmukler et al. . |
| 2,535,146 | 12/1950 | Lyons . |
| 2,608,762 | 9/1952 | Fox . |
| 2,644,233 | 7/1953 | Shmukler et al. .......................... 433/60 |
| 2,786,272 | 3/1957 | Lindley . |
| 2,982,025 | 5/1961 | Page . |
| 3,221,408 | 12/1965 | Scullin ....................................... 433/60 |
| 3,423,834 | 1/1969 | Irish . |
| 3,552,020 | 1/1971 | Weber ....................................... 433/57 |
| 3,653,126 | 4/1972 | Hansen . |
| 3,722,099 | 3/1973 | Jankelson . |
| 3,815,242 | 6/1974 | Martfay et al. ............................ 433/63 |
| 3,844,040 | 10/1974 | Willis . |
| 3,930,312 | 1/1976 | Daub ......................................... 433/61 |
| 3,975,489 | 8/1976 | Mercer ...................................... 264/222 |
| 4,169,314 | 10/1979 | Mercer et al. . |
| 4,337,039 | 6/1982 | Martin et al. .............................. 433/60 |
| 4,758,155 | 7/1988 | Marino ...................................... 433/61 |
| 5,007,829 | 4/1991 | Farrell ....................................... 433/61 |

*Primary Examiner*—Cary E. O'Connor
*Attorney, Agent, or Firm*—Trexler, Bushnell, Giangiorgi & Blackstone, Ltd.

[57] ABSTRACT

A dental articulator which is basic in construction and practical for use by dentists as a routine procedure in their general practices. The articulator includes a base platform for stabilizing the articulator in first and second positions on a work surface, a longitudinal support column attached to the base platform, upper and lower support arms connected to the support column, and may include quick-release couplings providing a firm, adjustable and quickly removable mount for stone teeth casts. The lower support arm pivots and the upper does not, to more accurately simulate human jaw movement.

16 Claims, 2 Drawing Sheets

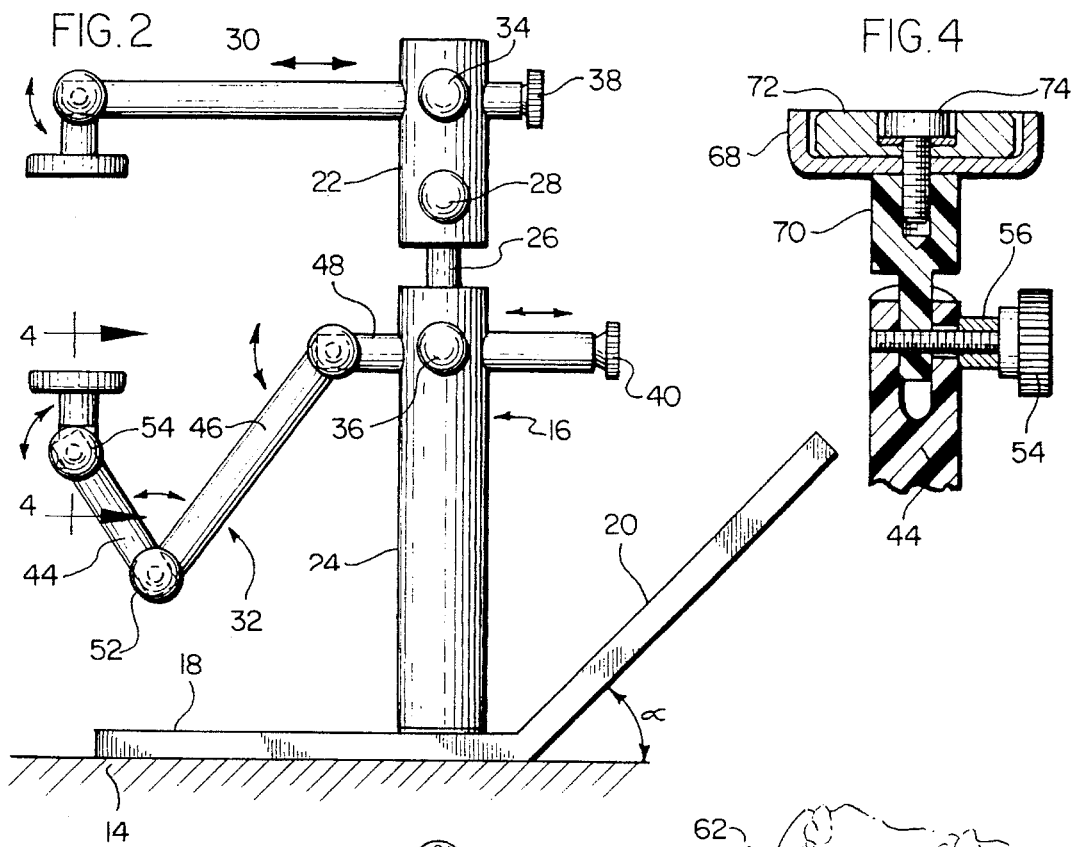
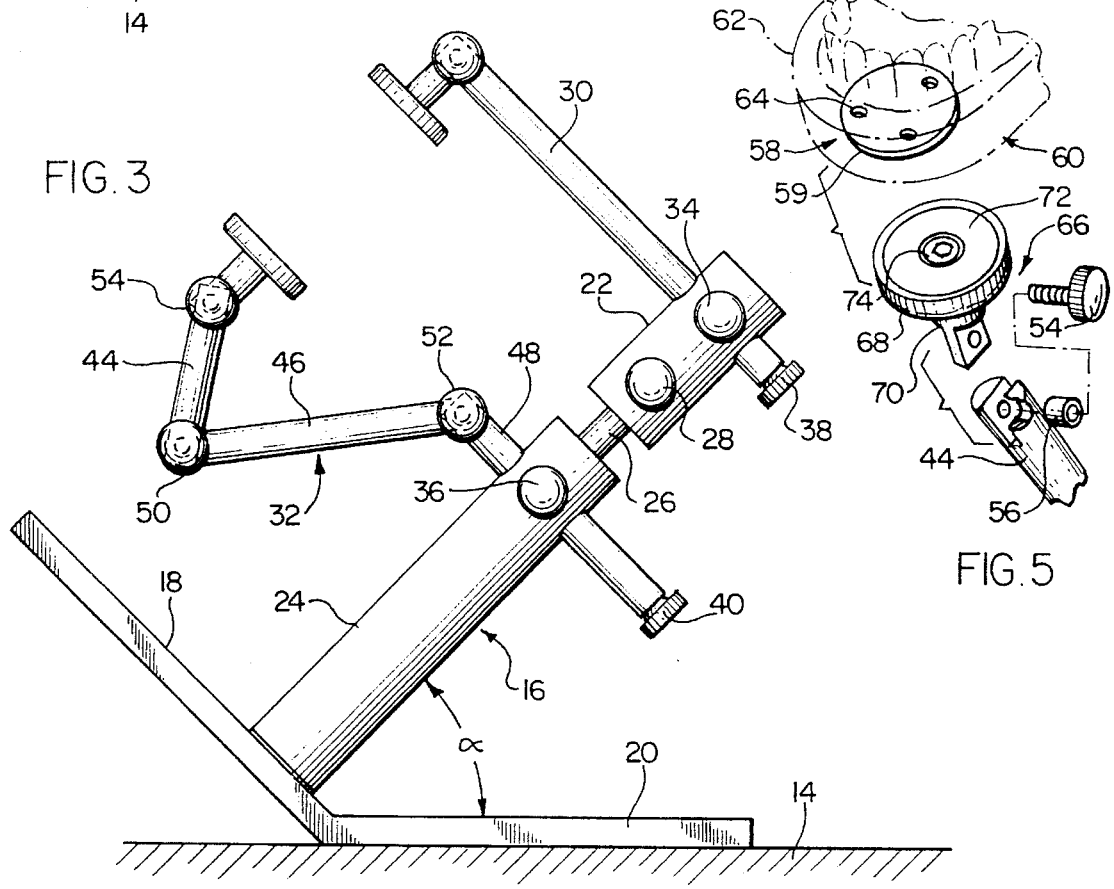

DENTAL ARTICULATOR

BACKGROUND OF THE INVENTION a. Field of the Invention

In general, this invention relates to a dental articulator. More specifically, this invention relates to a dental articulator which is fundamental in construction, practical for use on a regular basis, and more suitable for many of the functions performed by a traditional articulator.

b. Description of Related Prior Art

Traditional dental articulators have been in use for many decades. The primary function of a dental articulator is to replicate a patient's dentition and or edentulous areas via stone casts. The casts approximate each other in a manner that simulates the patient's natural tooth positioning. These casts are usually mounted in the centric occlusion position, meaning the most interdigitated position of the teeth. Ideally, however, the casts are mounted in the centric relation position. The centric relation position may be broadly described as the natural articulation of the patient's teeth when the mandibular condyles are in their terminal hinge position. This is the most superior position of the condyles in their fossa. The centric relation position is usually different from the centric occlusion position, which is the patient's most intercuspal tooth position. A shift in the jaw can usually be seen in going from the centric relation position into the centric occlusion position.

These mounted casts can be used for a variety of purposes. Preliminary or diagnostic models are used for treatment planning, patient education and dental student learning. Working models are used for restorative needs such as the fabricating crowns, bridges, dentures, splints, implant prosthesis and orthodontic appliances. Precise simulation of the jaw movements can also be a valuable tool in the education of dental students and patients alike.

Using a traditional articulator to perform these functions can be a very time consuming and complex endeavor. An hour or more can easily be spent to form and correctly mount teeth casts on most of the articulator instruments currently available. Moreover, because multiple plaster mixes of stone are needed to mount and groom the casts on a traditional articulator, in addition to the complex measurements and adjustments needed during the mounting process, the patient from whom the impressions were taken to form the cast mountings is usually no longer available for verifying the centric relation bite. Therefore, if the first formed cast mountings are inaccurate, the entire process must be repeated. Also, such traditional instruments are usually intricate mechanical devices which require a trained and experienced operator to obtain reliable data. As a result, most dentists see no practical use for traditional articulators in their work.

OBJECTS OF THE INVENTION

It is a general objective of the present invention to provide an improved dental articulator which is fundamental in construction and more practical and suitable for many uses. It is a more specific objective to provide an improved dental articulator which includes quick release couplings for mounting maxillary and mandibular teeth casts.

A related objective is to provide an improved dental articular which allows for practical verification of a patient's centric bite relation.

Another objective is to provide an improved dental articulator which includes a mandibular cast support arm which pivots similar to a human jaw.

Still another objective is to provide an improved dental articulator which includes a base platform enabling the articulator to be supported in more than one position on a work surface.

Other objects and advantages of the invention will become apparent upon reading the following details and description, and upon reference to the drawings. Throughout the description, like reference numerals refer to like parts.

SUMMARY OF THE INVENTION

Summarily stated, the present invention provides a dental articulator for mounting molded casts of teeth, which casts include a mounting surface and define an occlusal plane, the articulator comprising a base platform for stabilizing the articulator in a first position on a work surface, a longitudinal support column securely attached to the base platform, upper and lower support arms operatively connected with the support column. In one aspect, the articulator further includes at least one quick-release coupling for mounting a cast on a support arm such that the cast is firmly mounted and quickly removable. In another aspect, the lower support arm pivots about a point at or near the support column and the upper support arm does not pivot with respect to the support column, thereby substantially replicating a human jaw movement. In still another aspect, the invention includes a back platform integral with the base platform for stabilizing the articulator in a second position on a work surface.

BRIEF DESCRIPTION OF THE DRAWINGS

The features of the present invention which are believed to be novel are set forth with particularity in appended claims. The organization and manner of operation of the invention together with further objects and advantages thereof may best be understood by reference to the following descriptions taken in connection with the accompanying drawings, in which:

FIG. 2 is a side elevational view of the articulator in a first position on a work surface;

FIG. 3 is a view similar to FIG. 2 illustrating the articulator in a second position on a work surface;

FIG. 4 is a sectional view taken along line 4—4 of FIG. 2; and

FIG. 5 is an exploded view of a preferred form of a quick-release coupling of the present invention including an illustration of a tooth cast in phantom lines.

DETAILED DESCRIPTION OF THE PREFERRED EMBODIMENT

Figure 1:
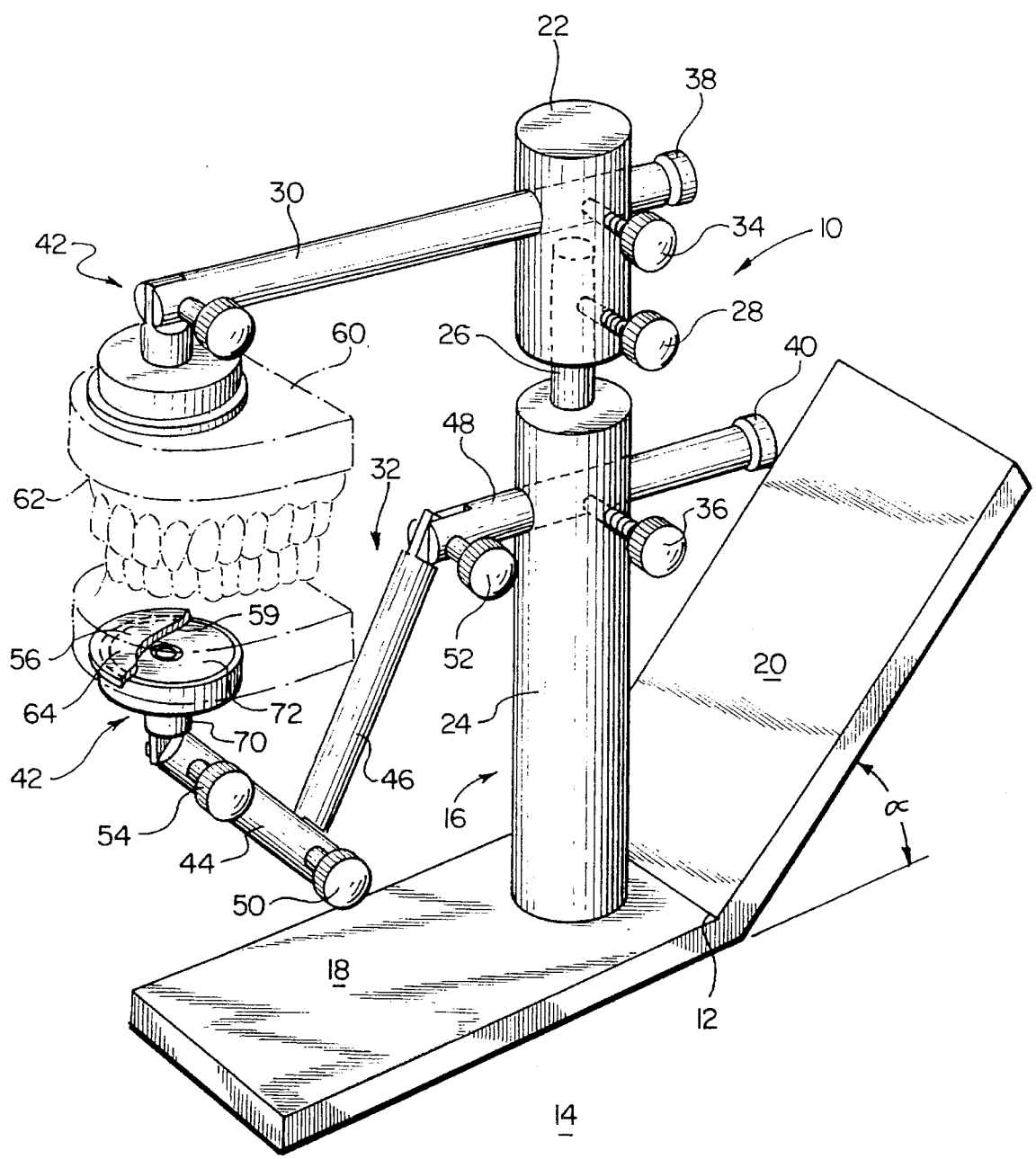
FIG. 1 is a perspective view of the improved dental articulator of the present invention.

While this invention may be susceptible to embodiment in different forms, there is shown in the drawings and will be described here in a specific embodiment with the understanding that the present disclosure is considered an exemplification of the principles of the invention and is not intended to limit the invention to that as illustrated.

Turning to FIG. 1, the improved articulator 10 of the present invention is shown in a first position on a work surface 14. Upon closer examination, it can be seen that the articulator 10 includes a base platform 12, having a longitudinal support column 16 which extends vertically upward from a location on a front section 18 of the base platform 12. Preferably, the support column 16 is affixed to the base platform 12 by means of a fastener (not shown) or in any other manner which would not permit the support column 16 to be readily detached from the base platform 12. As will be described in greater detail below, the base platform 12 also includes an integral back section 20 arranged at a predetermined angle $\propto$ with the horizontal work surface 14. It should be appreciated by those skilled in the art that the back section 20 could be connected to the base platform in a variety of manners and at a variety of angles, even adjustable if desired, and that such is intended to be included as falling within the scope of the preferred embodiment of the present invention.

Further, it should be apparent that the support column 16 includes a top segment 22 and a bottom segment 24 connected with a rod member 26. Interconnection with the rod member 26 allows the overall height of the support column 16 to be adjusted over a predetermined range, and permits the top segment 22 to swivel, both of which adjustments can be held in place with a locking screw 28.

Also included in the articulator 10 are an upper support arm 30 and a lower support arm 32 which, at the points of intersection with the main support column 16, extend substantially orthogonally through the support column 16 in bores formed therein. Thus, it should be readily apparent that both the upper support arm 30 and the lower support arm 32 can move transversely over a limited range and rotate with respect to the support column 16. In addition, locking screws 34, 36 are provided in the support column 16 to fix the positional relationship of the upper and lower support arms 30, 32, respectively, at selected positions. In addition, control knobs 38 and 40 are formed at the ends of the upper and lower support arms 30 and 32 nearest the support column 16 to facilitate the translational and rotational motion discussed.

Referring also now to FIG. 2, the upper support arm 30, as illustrated, extends in one piece and terminates at a remote end from the support column 16 where it connects with a quick-release coupling assembly 42. The lower support arm 32 also terminates at a remote end from the support column 16 where it connects to a quick-release coupling assembly 42. However, the lower support arm 32 is seen to include three joined sections referred to hereinafter as the forward portion 44, the intermediate portion 46 and the rear portion 48 of the lower support arm 32, the function of which will be explained in detail below. A locking screw 50 is provided for pivotally connecting (and maintaining at selected locations) the forward portion 44 with the intermediate portion 46. Another locking screw 52 performs a similar function with respect to the pivotal junction between the intermediate portion 46 and the rear portion 48. FIG. 4 is an enlarged view of yet another locking screw 54 used in conjunction with a coupling assembly 42, but it also provides a clear understanding of all of the pivotal interconnections between the multiple portions of the lower support arm 32, which operate in like manner. Specifically, a threaded bore is formed through the grooved-end of one member (forward portion 44, for example) and aligned with a similar threaded bore formed through a bladed-end of an adjacent member (the coupling assembly 42, for example). Locking screw 54 is then selectively tightened down onto a sleeve member 56 which bears against the pivoting blade-groove junction to hold the joined members in the exact position desired. Once again, however, it should be obvious to those skilled in the art that the same result can be accomplished with several known means, all of which are intended to fall within the ambit of the present invention.

In accordance with one of the main features of the present invention, attention is now also directed to FIG. 5 which provides an exploded perspective view of a quick-release coupling assembly 42. In a preferred embodiment, the first member 58 of the quick-release coupling assembly 42 includes a mounting plate 59 which is embedded into the mounting surface 60 provided on a stone teeth cast 62 (shown in phantom lines in FIGS. 1 and 5). Protrusions 64 are also included with the mounting plate 59 and function to secure the plate in the plaster cast 62. The mounting plate 59 is intended to be placed on the cast 62 before the plaster has completely hardened. It should be noted that securing the mounting plate 59 directly to the cast 62 as described, completely eliminates the need to conduct any additional plaster pours, such as those required to secure a guide plate used with a traditional articulator to a stone cast. It is not uncommon to require at least two separate plaster pours to attach a guide plate which, when considering this procedure must be performed for both the maxillary and mandibular casts, takes a significant amount of time.

A second member 66 of the quick-release coupling assembly 42 includes a magnet housing 68 having a coupling arm extension 70 (attached thereto, or integrally formed therewith), for pivotally connecting the second member 66 to a support arm 30 or 32 by means of a blade-groove connection and locking screw, as described above. It should be apparent that a quick-release coupling assembly 42 is ideally used to mount cast 62 on both the upper and lower support arms 30 and 32, and that the present discussion applies equally to the assembly 42 used at both such locations.

Returning to FIG. 5, the second member 66 of the quick-release coupling assembly 42 is also shown to include a magnet 72 mounted in the magnet housing 68 by way of a set screw 74. It should be obvious to a person having ordinary skill in the art that, in a modified version of the invention, the magnet 72 could just as easily be included in the first member 58 of the quick-release coupling assembly 42, and the mounting plate 59 could be secured in the housing 68. Most importantly, the quick-release coupling assembly 42 as described provides a firm mounting for a cast 62 which is quickly and easily removed. So mounted, a cast 62 is also easily adjustable in the occlusal plane, defined by the tooth surface of a cast, opposite the mounting surface 60.

Adjustment in the occlusal plane can quickly correct errors in the state of intercuspation of the mounted cast to best replicate the natural articulation in question.

Another important aspect of the present invention is best understood with reference to FIG. 1, wherein it is clearly illustrated that the lower support arm 32 is made up of three joined parts referred to above as the forward portion 44, the intermediate portion 46 and the rear portion 48. Moreover, as can easily be envisioned, pivotal adjustment of the lower support arm 32 by use of the locking screws 52, for example, can operate the articulator to accurately simulate the movement of a human jaw. As is true in the case of an actual human jaw, but not in the case of a traditional articulator, the upper support arm 30 does not pivot with respect to the longitudinal access of the vertical support column 16.

On a related topic, dividing the lower support arm 32 into the three portions 44, 46 and 48 as described, causes the opening-closing arc of motion through which a cast 62 moves to occur entirely below the occlusal plane defined when two mounted casts 62 are in the centric occlusion position. This is the patient's most intercuspal tooth position. In this manner, any interference which might otherwise occur between the two surfaces of the cast 62 during the operation of the articulator is eliminated. All movement of the cast 62 mounted on a lower support arm 32 occurs downward and inward from the mating cast during the opening-closing arc. Pivoting of the lower arm 32 during the opening-closing arc normally occurs at or near the support column 16, such as at the location surrounding the locking screw 54 in FIG. 1.

It should also be noted that the upper and lower support arms 30 and 32 are constructed of a somewhat flexible material to enable side movement of the mounted cast 62 to help in fabricating excursive shapes and contours of restorations. In addition, orthodontists can use the articulator 10 as described to check diagnostic casts and treatment progress. Currently, the accepted mode of evaluating orthodontic casts is by placing hand held, unmounted models together in a "heel-to-heel" manner, which cannot check for excursive bite interferences or verify centric relations occlusion. Oral surgeons can also benefit through use of the articulator by quickly mounting diagnostic casts in treatment evaluation prior to orthognathic surgery.

Yet another important aspect of the invention is best illustrated by reference to FIGS. 2 and 3. As briefly described above, these figures illustrate that the base platform 12 is comprised of two distinct sections, the front 18 and the back 20. In FIG. 2, the articulator is supported by the front section 18 on a work surface 14 in a more traditional position wherein the support column 16 is substantially vertical and substantially perpendicular to the work surface 14. In FIG. 3, however, the articulator 10 is supported by the back section 20 of the base platform 12 such that teeth casts 62 mounted on the articulator will be orientated very similar to the position of a patient's teeth under normal examination procedures by a dentist.

As illustrated, when the articulator 10 is supported on the back section 20, the support column 16 is held at an angle ∝ of substantially 45°. In addition, in the preferred embodiment, the back section 20 is integrally formed with the front section 12, both of which are made of plastic. Once again, it should be obvious to those skilled in the art that modifications can be made to both the angle and the manner of attaching the front and back sections together. In fact, a modified version of the invention could include a mechanism to selectively change the angle over a predetermined range to accommodate various applications. Obviously, other materials could also be used.

While a preferred embodiment of the invention is shown and described, it is envisioned that those skilled in the art may devise modifications of the present invention without departing from the spirit and scope of the appended claims.

The invention is claimed as follows:

1. A dental articulator for mounting molded casts of teeth having a mounting surface and defining an occlusal plane, said articulator comprising:

a. a base platform for stabilizing the articulator in a first position on a work surface;

b. a longitudinal support column securely attached to the base platform;

c. upper and lower support arms of predetermined length operatively connected with the support column;

d. at least one quick-release coupling for mounting a cast on a support arm such that the cast is firmly mounted and quickly removable;

e. wherein said quick-release coupling further comprises a first member mounted directly to the mounting surface of said cast, and a second member connected to said support arm, said connection occurring along a connecting plane parallel to said occlusal plane, said coupling allowing for fully traversable and rotational adjustmental movement of the mounted cast in and along said connecting plane.

2. A dental articulator as recited in claim 1, wherein at least one of said first and second members of said quick-release coupling includes a magnet.

3. A dental articulator as recited in claim 1, wherein said quick-release coupling further comprises a coupling arm for pivotally connecting to a support arm.

4. A dental articulator as recited in claim 1, wherein at least some portion of the lower support arm pivots about a point at or near the support column and the upper support arm does not pivot with respect to the support column, thereby substantially replicating a human jaw movement.

5. A dental articulator as defined in claim 4, wherein pivoting said portion of said lower support arm defines an opening-closing arc for a mounted cast which occurs entirely below the occlusal plane of said mounted cast when the cast is in a centric occlusion position.

6. A dental articulator as recited in claim 1, wherein the base platform further comprises an integral back platform for stabilizing the articulator in a second position on the work surface.

7. A dental articulator as recited in claim 6, wherein the support column is held at an angle of substantially 45° with respect to the work surface.

8. A dental articulator as recited in claim 1, wherein said lower support arm is divided into more than one portion each pivotally connected in a selectively releasable manner with another.

9. A dental articulator as recited in claim 1, wherein the support column is provided with means for selectively adjusting a vertical separation existing between said upper and lower support arms.

10. A dental articulator for mounting molded casts of teeth having a mounting surface and defining an occlusal plane when mounted in the articulator, said articulator comprising:

a. a base platform for stabilizing the articulator in a first position on a work surface b. a support column securely attached to the base platform c. upper and lower support arms operatively connected with the support column d. a cast coupling located on each of the upper and lower support arms for mounting a cast on each of said support arms in an operable manner;

e. wherein at least some portion of the lower support arm pivots about a point at or near the support column to define an opening-closing arc for a mounted cast which occurs entirely below the occlusal plane and wherein the upper support arm does not pivot with respect to the support column thereby substantially replicating a human jaw movement; and f. wherein said lower support arm is divided into more than one portion each pivotally connected in a selectively releasable manner with another.

11. A dental articulator as recited in claim 10, wherein the cast couplings further comprise a first member connected to said support arm and a second member mounted directly to the mounting surface of said cast, said coupling allowing for adjustmental movement of the cast in the occlusal plane.

12. A dental articulator as recited in claim 11, wherein at least one of said first and second members of said cast coupling includes a magnet.

13. A dental articulator as recited in claim 11 wherein the cast couplings further comprise quick-release devices so that the cast can be firmly mounted and quickly removed from the upper and lower support arms.

14. A dental articulator as recited in claim.13 wherein at least one of the quick-release devices comprises a magnetically-linked member pair.

15. A dental articulator for mounting molded casts of teeth having a mounting surface and defining an occlusal plane, said articulator comprising:

a. a base platform for stabilizing the articulator in a first position on a work surface;
  b. a longitudinal support column securely attached to the base platform;
  c. upper and lower support arms of predetermined length operatively connected with the support column;
  d. at least one quick-release coupling for mounting a cast on a support arm such that the cast is firmly mounted and quickly removable;
  e. wherein said quick-release coupling further comprises a first member mounted directly to the mounting surface of said cast, and a second member connected to said support arm, said coupling allowing for adjustmental movement of the cast in the occlusal plane, and;
  f. wherein means are provided to allow the upper support arm to selectively traverse and rotate with respect to the main support column.

16. A dental articulator as recited in claim 15, wherein said lower support arm is divided into more than one portion each pivotally connected in a selectively releasable manner with another, and; wherein a portion of the lower support arm is connected with the support column and provided with means to selectively traverse and rotate with respect to the main support column.

* * * * *